US00PP31773P3

(12) United States Plant Patent
Pírez

(10) Patent No.: US PP31,773 P3
(45) Date of Patent: May 19, 2020

(54) STRAWBERRY PLANT NAMED 'RIKAS FNM'

(50) Latin Name: ***Fragaria* x *ananassa***
Varietal Denomination: Rikas FNM

(71) Applicant: Fresas Nuevos Materiales S.A., Huelva (ES)

(72) Inventor: Antonio Refoyo Pírez, Huelva (ES)

(73) Assignee: Fresas Nuevos Materiales S.A., Huelva (ES)

( * ) Notice: Subject to any disclaimer, the term of this patent is extended or adjusted under 35 U.S.C. 154(b) by 0 days.

(21) Appl. No.: 15/998,037

(22) Filed: Jun. 19, 2018

(65) Prior Publication Data

US 2019/0037752 P1 Jan. 31, 2019

(30) Foreign Application Priority Data

Jul. 26, 2017 (ES) ..... PBR 20175320

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 5/08; A01H 5/0893; A01H 5/0831; A01H 6/74; A01H 6/7409
See application file for complete search history.

(56) References Cited

PUBLICATIONS

International Code of Nomenclature for Cultivated Plants Ninth Edition 2016, retrieved on May 21, 2019, retrieved from the Internet at https://www.ishs.org/sites/default/files/static/ScriptaHorticulturae_18.pdf, cover page, ii-iv and 29. (Year: 2016).*
Upov Pluto Plant Variety Database May 13, 2019, retrieved on May 13, 2019, retrieved from the Internet at www3.wipo.int/pluto/user/en/index.jsp, 2 pp. (Year: 2019).*

* cited by examiner

*Primary Examiner* — June Hwu
(74) *Attorney, Agent, or Firm* — Cooley LLP

(57) ABSTRACT

The present invention provides a new and distinct strawberry plant designated as 'Rikas FNM', which originate from seed produced by manual cross between 'E64' and '86N'. The new strawberry is a day-neutral with a long, conical, glossy and a light red color fruit. This new strawberry is characterized by a fruit of excellent quality, long shelf-life and high value of Brix degrees.

5 Drawing Sheets

Botanical designation: *Fragaria* x *ananassa* Duchesne.
Varietal denomination: 'Rikas FNM'.

CROSS REFERENCE TO RELATED APPLICATIONS

This application claims priority to, and the benefit of the Spanish Plant Breeder's Right (PBR) Application No. 20175320, filed on Jul. 26, 2017, titled "Oficina Española de Variedades Vegetales", directed to the strawberry variety in the present application (named as 'A13-27N-3' in the PBR application), which is herein incorporated by reference in its entirety.

BACKGROUND OF THE INVENTION

The present invention relates to a new and distinct day-neutral strawberry variety designated as 'A13-27N-3' by the breeder, and later named 'Rikas FNM'.

'Rikas FNM' was created in a breeding program and is the result of a controlled-cross between the experimental short day female parent designated 'E64' and day-neutral experimental selection '86N', made by the Inventor and was first fruited in Gibraleón, (Huelva, Spain) growing fields. From the beginning and during testing, the plant was designated 'A13-27N-3'.

This new variety was asexually reproduced via runners (stolons) by the inventor at Gibraleón, Huelva, Spain. Asexual propagules from the original source have been tested in Gibraleón, Moguer and Palos de la Frontera (Huelva, Spain) growing fields and to a limited extent, grower fields in high elevation in Arevalo, Avila, Spain. The properties of this variety were found to be transmissible by such asexual reproduction. This cultivar is stable and reproduces true to type in successive generations of asexual reproduction.

SUMMARY OF THE INVENTION

The present invention relates to a new and distinct strawberry variety. The varietal denomination of the new variety is 'Rikas FNM'. Among the characteristics which are believed to distinguish the new variety from other varieties are a combination of traits which include the day length that is a day neutral; the plant growth habit it is upright and open with light density of foliage; the vigour of the plant is high, the inflorescence appears at level with the foliage; the fruit color is light red, the fruit is very sweet, conical-shaped, very firm, medium size fruit and long shelf-life.

BRIEF DESCRIPTION OF THE DRAWING

The accompanying color photographs and traits show typical specimens of the new cultivar at various stages of development as nearly true as it is possible to make in color reproductions. The pictures were taken during in April in Huelva, Spain.

DETAILED DESCRIPTION OF THE INVENTION

Figure 1:
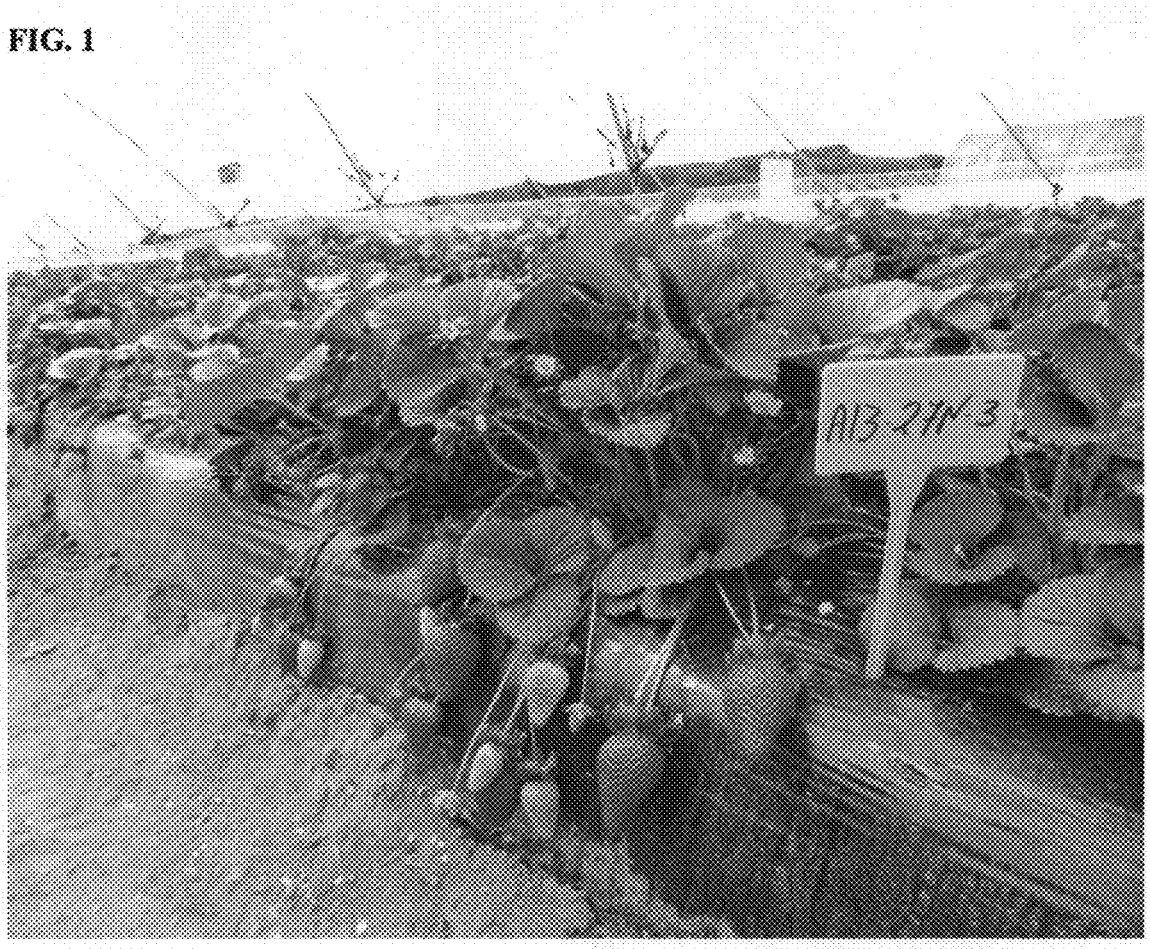
FIG. 1 shows overall plant habit including fruit at various stages of development.
Figure 2:
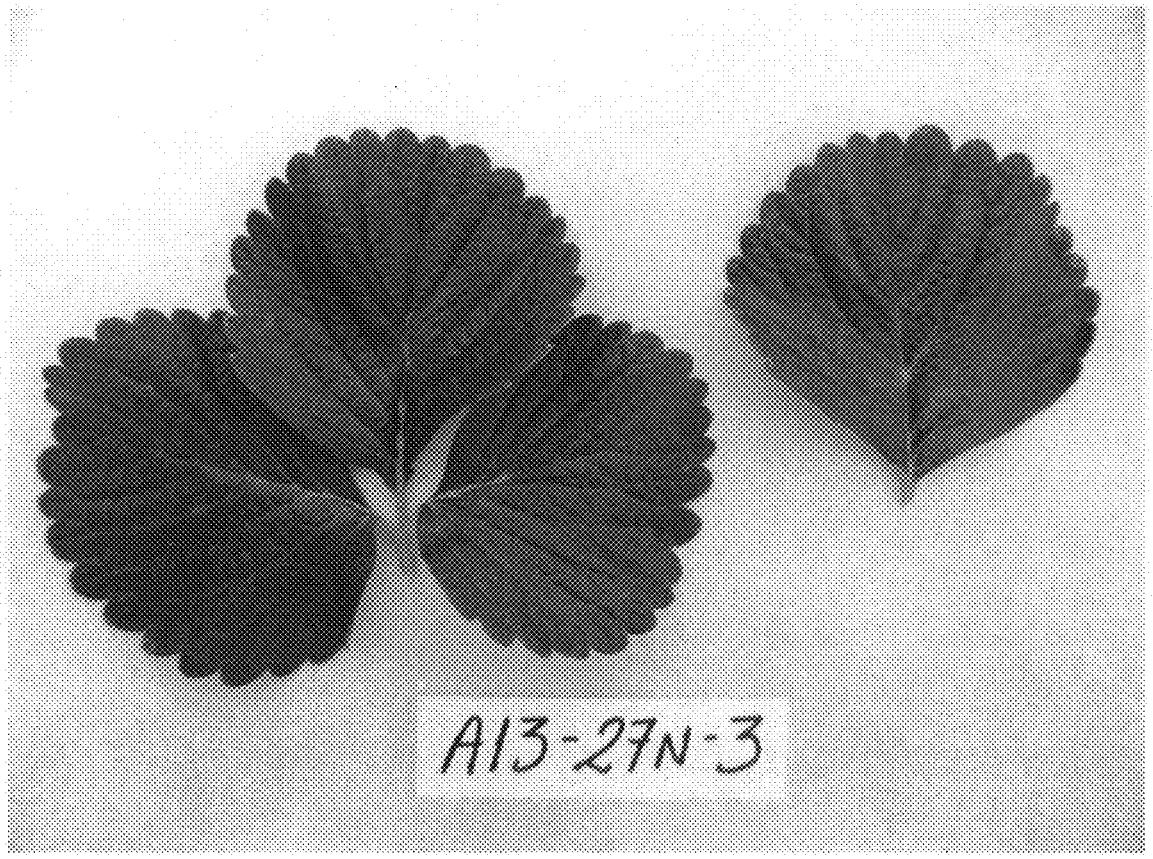
FIG. 2 shows leaves of the plant with three leaflets.
Figure 3:
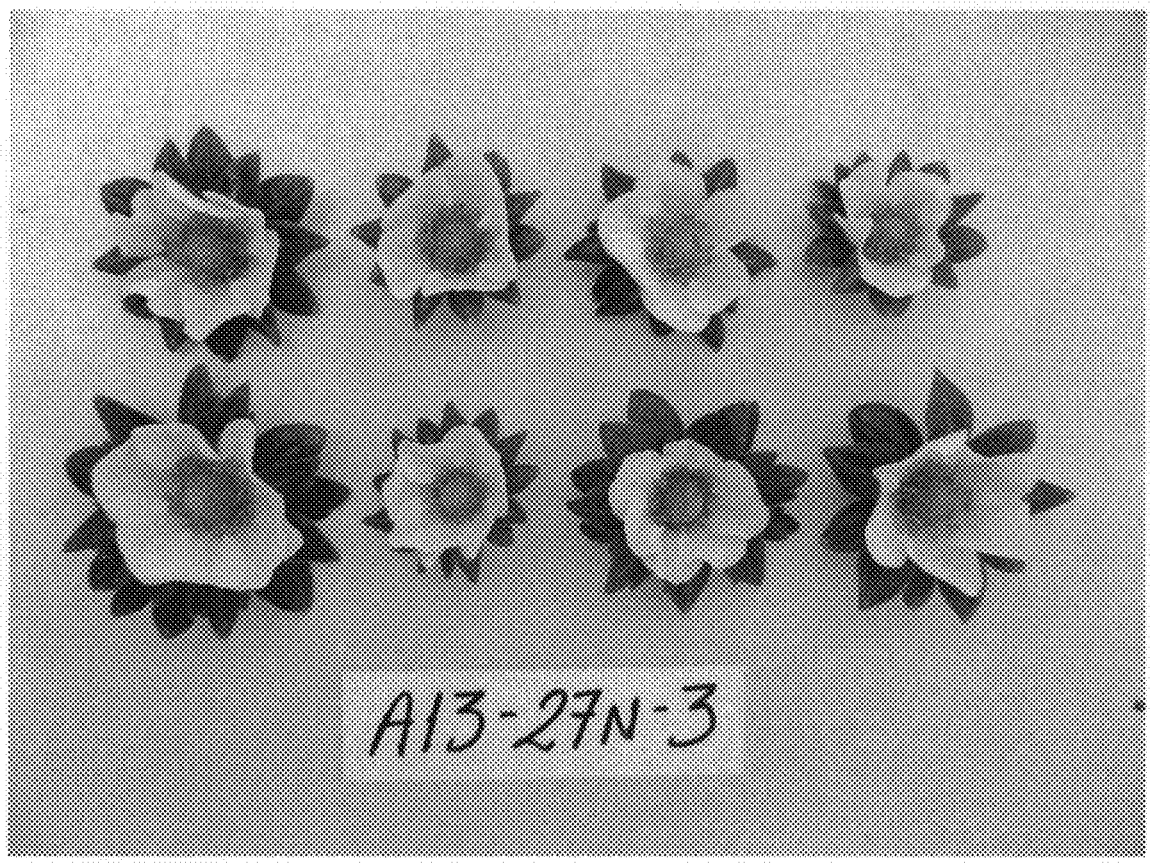
FIG. 3 shows the upperside of several flowers.
Figure 4:
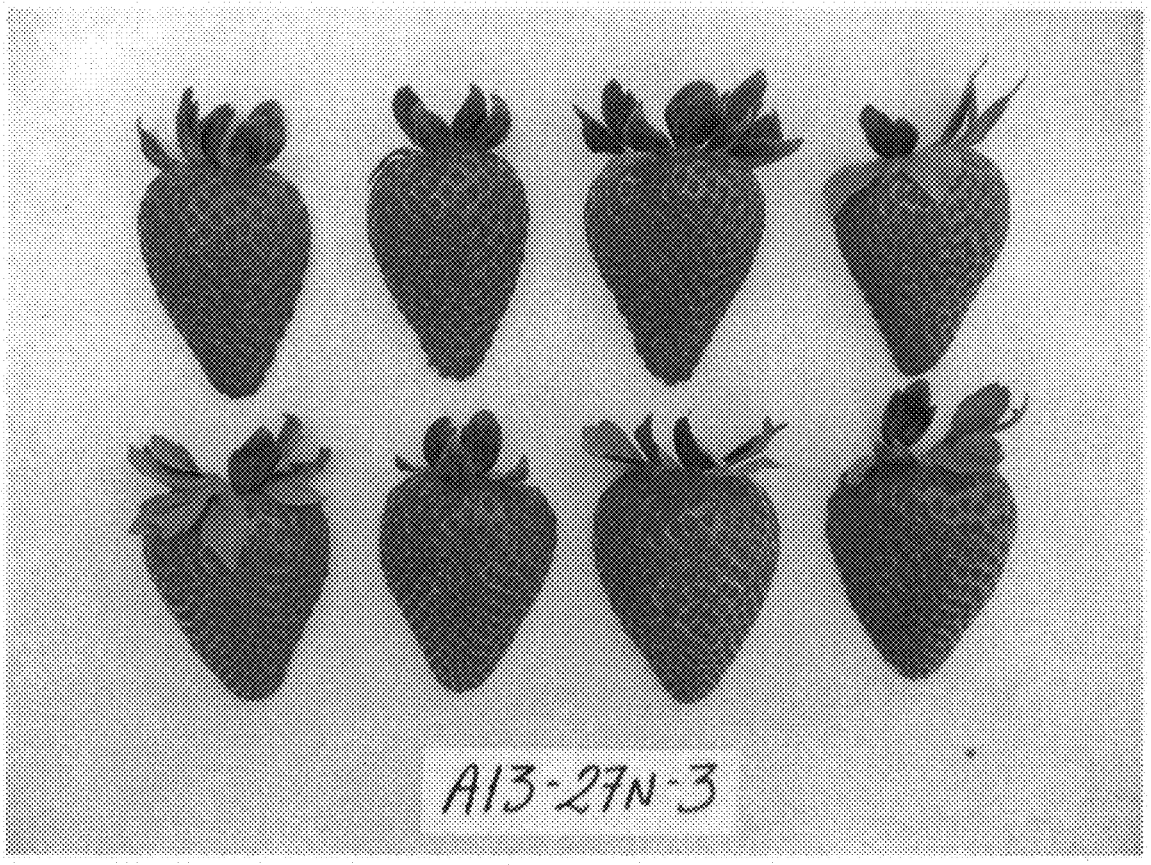
FIG. 4 shows the whole fruit.
Figure 5:
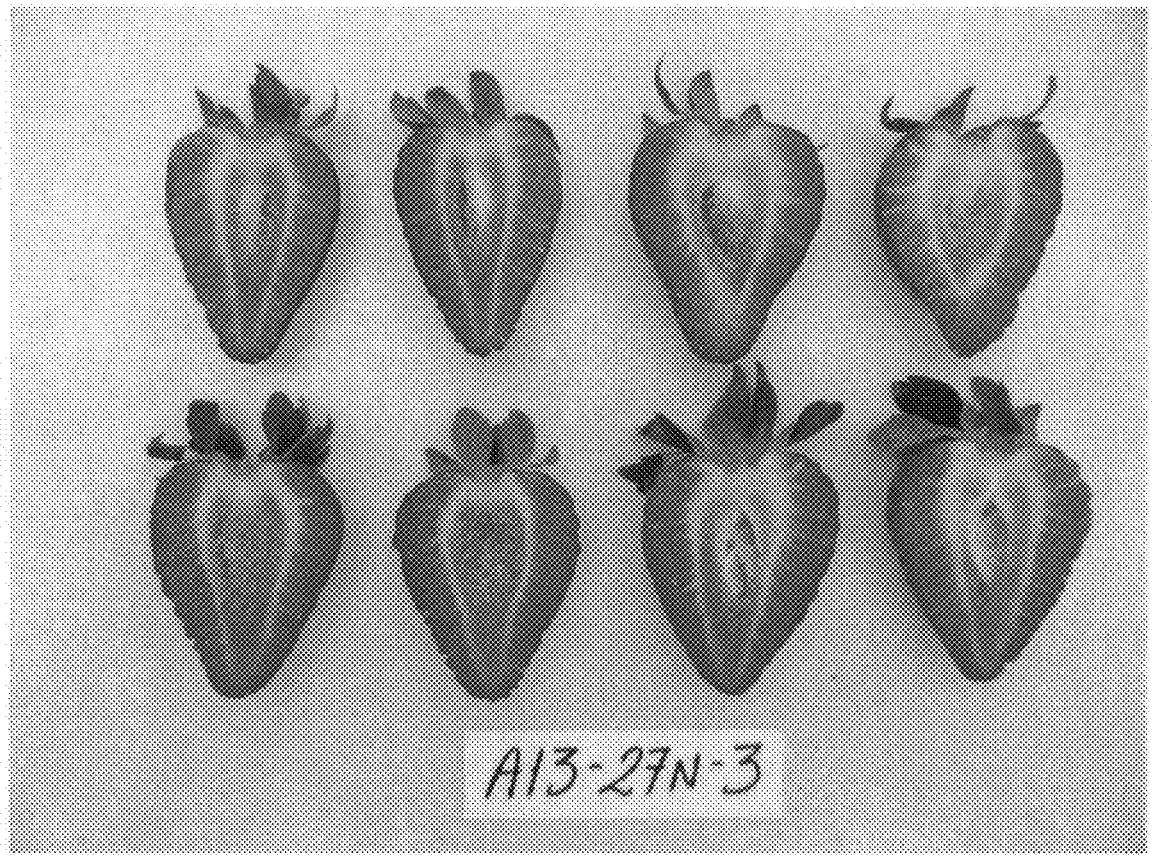
FIG. 5 shows the fruit in longitudinal cross-section.

This invention relates to a new and distinctive day-neutral variety named 'Rikas FNM'. 'Rikas FNM' produces fruit regardless of the day length when cultivated appropriately in temperate climates.

This cultivars is primarily adapted to the climate and growing conditions of the South of Spain (Huelva)

'Rikas FNM' is a vigorous plant, upright and open which facilitates the fruit harvesting. It produces long and mainly unbranched peduncles. 'Rikas FNM' produces a fruit of medium size, with a long conical shape, a light red color and a glossy fruit. The fruit has an excellent quality, the firmness is high and has a high value of Brix degrees. The fruit of 'Rikas FNM' has an excellent taste and appearance. Also noteworthy in the new variety 'Rikas FNM' is the great shelf-life that the fruit presents due to its firm flesh together with achenes level with the flesh and skin very resistant to bruising. 'Rikas FNM' produces a moderate amount of stolons which facilitates its multiplication.

'Rikas FNM' is moderately resistant to the most frequent diseases in Huelva (Spain). Specifically, it is moderately resistant to powdery mildew (*Podosphaera macularis*), Verticillium wilt (*Verticillium dahliae*) and Phytophthora crown rot (*Phytophthora cactorum*). 'Rikas FNM' is relatively tolerant to pests such as aphids and spider mites.

The results of production and Brix degrees of the variety 'Rikas FNM' compared to the variety 'San Andreas' (U.S. Plant Pat. No. 19,975) are shown below (Table 1). The results that are shown come from a trial located in Gibraleón (Huelva, Spain). Trial was a randomized complete block design with three repetitions and 40 plants per plot. The planting date was Oct. 20, 2016 and was cultivated until May 25, 2017. It was cultivated under standard conditions of strawberry cultivation in Huelva, Spain.

TABLE 1

| Variety | Avg. Yield | 1st Quality | Early Yield | Brix | P. Mildew |
|---|---|---|---|---|---|
| Rikas FNM | 1002 | 86 | 420 | 9, 7 | 3, 3 |
| San Andreas | 772 | 84 | 341 | 8, 8 | 3, 1 |
| LSD(5%) | 196 | 4 | 103 | 1, 0 | 0, 2 |
| LSD(1%) | 265 | 5 | 140 | 1, 3 | 0, 2 |

Table 1. Fruit production and Brix degrees data of the new variety 'Rikas FNM' and 'San Andreas'. Each value is the result of the average of three repetitions of 40 plants. Avg. Yield, total commercial yield in grams by plant; 1st Quality, percentage of first class fruit; Early Yield, early production (before March 31) in grams by plant; brix, Brix degrees; P. Mildew, powdery mildew (Sphaerotheca macularis) resistance score, 5 the best. LSD(5%) and LSD(1%) Least Significant Difference between the means at P≤0.05 and 0.01 respectively.

The fruit of 'Albion' has clear differences with respect to the fruit of the new variety 'Rikas FNM'. The variety 'Albion' shows a fruit with a darker red, a larger fruit and the more sunken achenes than the fruit of the variety 'Rikas FNM'.

The following traits in combination distinguish strawberry variety 'Rikas FNM' from known strawberry varieties ("Table 1", "Table 2. General", "Table 3. Leaf", "Table 4. Petiole, the bract, and the stipule", "Table 5. Inflorescence", "Table 6. Runner (Stolon)" and "Table 7. Fruit"). We use as standard variety for comparison 'Albion' (U.S. Plant Pat. No. 16,228). The traits were measured in Huelva (Spain), in April 2017. When we made the measurements, the plant was 6 months old. Fresh bare root plants were used for planting in October 2016. Plants for the botanical measurements in the present application were grown as annuals. Any color references are made to The Royal Horticultural Society Color Chart, 1995 Edition, except where general terms of ordinary dictionary significance are used.

TABLE 2

General

| Characteristic | Rikas FNM | Albion |
|---|---|---|
| Plant Growth Habit) | Upright | Semi-upright |
| Day length | Neutral | Neutral |
| Density of foliage | Light | Medium |
| Plant vigor | High | Moderate |
| Average plant height | 20.6 cm | |
| Average plant spread | 29.8 cm | |

TABLE 3

Leaf

| Characteristic | Rikas FNM | Albion |
|---|---|---|
| Terminal leaflet length/width ratio | 1.07 | 1.20 |
| Leaf average length | 15.4 cm | |
| Leaf average width | 16.8 cm | |
| Glossiness | Medium | |
| Leaf color upper side | 141A to 141B | |
| Leaf color lower side | 138B to 139C | |
| Leaf apex shape | Rounded | |
| Leaf base shape | Obtuse | |
| Leaf blistering | Medium | Weak |
| Terminal Leaflet margin | Serrate to crenate | Crenate |

TABLE 4

Petiole, the bract, and the stipule

| Characteristic | Rikas FNM | Albion |
|---|---|---|
| Petiole length (cm) | 19 | 17 |
| Petiole diameter (cm) | 0.33 | 0.42 |
| Petiole pose of hairs | Outwards | Slightly Outwards |
| Petiole color (color code) | RHS: N144C | RHS: N144A |
| Stipule length (cm) | 2.3 | 2.7 |
| Stipule width (cm) | 0.6 | 1.0 |
| Stipule pubescence | Weak | Weak |
| Stipule anthocyanin presence or absence | Absence | Absence |
| Stipule color (color code) | RHS: 149C | RHS: N144C |
| Pedicel color (color code) | RHS: 144C | RHS: 144A |
| Attitude of hairs on petiole and pedicel | Upwards | Slightly Upwards |

TABLE 5

| Inflorescence | | |
|---|---|---|
| Characteristic | Rikas FNM | Albion |
| Inflorescence position relative to foliage | Even | Below |
| Petal spacing (e.g., overlapping etc.) | Overlapping | Touching |
| Petal number per flower | 5 | 6 |
| Upper and lower Petal color (color code) | RHS: NN155D | RHS: NN155D |
| Peduncle size | Long | Medium |
| Flower diameter | 2.4 cm | 2.8 cm |
| Calyx diameter relative to corolla | Much larger | Much larger |
| Sepal shape (e.g., Elliptical, etc.) | Elliptical | Elliptical |
| Sepal margin (e.g., entire, etc.) | Entire | Entire |
| Sepal number per flower | 12 | 10 |
| Number of stamen | 24 | 28 |
| Anther color (color code) | RHS: 2A | RHS: 2A |
| Time of flowering | November 30th | November 30th |
| Shape and color of stigma | Yellow | Orange |
| Color and length of style | Yellow, 1.9 mm | Green 1.2 mm |
| Color of the ovary | Green | White |
| Shape, size and color of anther | Oval, 1.9 mm, Yellow | Oval, 2.1 mm, Yellow |
| Color and amount (scarce, moderate or abundant) of pollen | Yellow Abundant | Yellow Abundant |
| Length and color of filament | 3.3 mm, Green | 4.2 mm, Green |

TABLE 6

| Runner (Stolon) | | |
|---|---|---|
| Characteristic | Rikas FNM | Albion |
| Stolon anthocyanin (color code) | RHS: N144D | RHS: N144B |
| Stolon pubescence | Sparse | Medium |
| Stolon color (color code) | RHS: 149B | RHS: N144C |

TABLE 7

| Fruit | | |
|---|---|---|
| Characteristic | Rikas FNM | Albion |
| Fruiting truss length | 11 cm | 7 cm |
| Characteristic | Rikas FNM | Albion |
| Number of fruit per truss | 3 | 6 |
| Truss color | RHS: 144A | RHS: N144A |
| Fruit length (cm) | 4.2 | 4.2 |
| Fruit width (cm) | 3.6 | 3.6 |
| Fruit skin color (color code) | RHS: 33A | RHS: 34A |
| Fruit flesh color excluding core | RHS: 33C | RHS: N25A |
| Fruit length/width ratio | 1.2 | 1.2 |
| Fruit weight (g) | 28 | 28 |
| Relative fruit size | Medium | Large |
| Predominant fruit shape | conical | conical |
| Position of achenes | even | below |
| Achene color (color code) | RHS: 9A | RHS: 11A |
| Diameter of calyx (cm) | 3.6 | 3.9 |
| Color of calyx (color code) | RHS: 143A | RHS: 141A |
| Color of the flesh | Light Red | Medium Red |
| Distribution of flesh color | Uniform | Some white center |
| Sweetness (by brix) | 9.3 | 7.4 |
| Type of bearing | day neutral | day neutral |
| Firmness | Firm | Medium |
| Storage Longevity | 10-12 days | 8-10 days |
| Fruit evenness of surface | Even | Even |
| Width of band without achenes | Absent or very narrow | Absent or very narrow |
| Adherence of calyx to fruit | Medium | Medium |
| Color Core | Light red (RHS: 33B) | Light red (RHS: 23H) |
| Cavity Size | Small | Medium |

The invention claimed is:

1. A new and distinct cultivar of strawberry plant having the characteristics substantially as described and illustrated herein.

* * * * *